United States Patent

Mine et al.

[11] Patent Number: 5,968,413
[45] Date of Patent: Oct. 19, 1999

[54] ANTI-FERROELECTRIC LIQUID CRYSTAL COMPOUNDS

[75] Inventors: Takakiyo Mine; Tomoyuki Yui; Masahiro Johno; Hiroshi Mineta, all of Tsukuba, Japan

[73] Assignee: Mitsubishi Gas Chemical Company, Inc., Tokyo, Japan

[21] Appl. No.: 09/013,912

[22] Filed: Jan. 27, 1998

[30] Foreign Application Priority Data

Jan. 27, 1997 [JP] Japan .................................. 9-012520

[51] Int. Cl.$^6$ ................. C09K 19/12; C09K 19/20; C07C 69/76; C07C 22/08
[52] U.S. Cl. .................. 252/299.65; 560/65; 560/83; 570/129; 252/299.67
[58] Field of Search ............ 252/299.65, 299.67; 570/129; 560/65, 83

[56] References Cited

U.S. PATENT DOCUMENTS

| | | | |
|---|---|---|---|
| 5,108,650 | 4/1992 | Koden et al. | 252/299.01 |
| 5,352,382 | 10/1994 | Johno et al. | 252/299.65 |
| 5,702,637 | 12/1997 | Johnson et al. | 252/299.61 |
| 5,705,094 | 1/1998 | Takeuchi et al. | 252/299.01 |
| 5,716,545 | 2/1998 | Kikuchi et al. | 252/299.65 |
| 5,723,069 | 3/1998 | Mineta et al. | 252/299.67 |

FOREIGN PATENT DOCUMENTS

| | | |
|---|---|---|
| 0497297 | 8/1992 | European Pat. Off. . |
| 0737733 | 10/1996 | European Pat. Off. . |
| 64-3154 | 1/1989 | Japan . |
| 1213390 | 8/1989 | Japan . |
| 1316339 | 12/1989 | Japan . |
| 1316367 | 12/1989 | Japan . |
| 1316372 | 12/1989 | Japan . |
| 2-28128 | 1/1990 | Japan . |
| 2225434 | 9/1990 | Japan . |
| 2229128 | 9/1990 | Japan . |
| 3292388 | 12/1991 | Japan . |

OTHER PUBLICATIONS

A.D.L. Chandani, et al., "Tristable Switching in Surface Stabilized Ferroelectric Liquid Crystals with a Large Spontaneous Polarization", Japan Journal of Appl. Physics, 27(5), L729–L732 (May 1988).

A.D.L. Chandani, et al., "Novel Phases Exhibiting Tristable Switching", Japan Journal of Appl. Physics, 28(7), L1261–L1264 (Jul. 1989).

A.D.L. Chandani, et al., "Antiferroelectric Chiral Smectic Phases Responsible for the Tristable Switching in MHPOBC", Japan Journal of Appl. Physics, 28(7), L1265–L1268 (Jul. 1989).

M. Johno, et al. "Smectic Layer Switching by an Electric Field in Ferroelectric Liquid Crystal Cells", Jap. Jour. Appl. Phys. 28(1), L119–L120 (Jan. 1989).

M. Johno, et al., Correspondence between Smectic Layer Switching and DC Hysteresis of Apparent Tilt Angle in an Antiferroelectric Liquid Crystal Mixture, Jap. Jour. Appl. Phys., 29(1), L111–L114 (Jan. 1990).

Y. Suzuki, et al., "New Fluorine–containing Ferroelectric Liquid Crystal Compounds Showing Tristable Switching", Liquid Crystals, 6(2), 167–174 (1989).

Primary Examiner—Shean C. Wu
Attorney, Agent, or Firm—Sherman and Shalloway

[57] ABSTRACT

Novel anti-ferroelectric liquid crystal compounds of the formula (1),

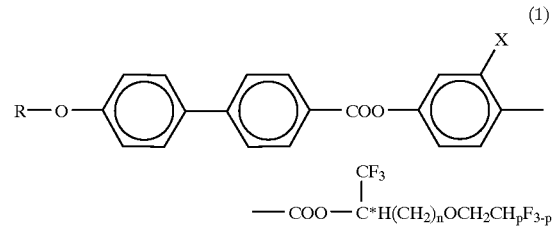

wherein R is a linear alkyl group having 6 to 12 carbon atoms, X is a hydrogen atom or a fluorine atom, n is an integer of 2 to 7, p is an integer of 0 to 2 and C* is an asymmetric carbon atom. The above anti-ferroelectric liquid crystal compounds have an anti-ferroelectric phase in a broad temperature range and have a low melting point, so that they can be advantageously used as a main component for a practically valuable liquid crystal material or as a component for a liquid crystal composition.

4 Claims, No Drawings

ANTI-FERROELECTRIC LIQUID CRYSTAL COMPOUNDS

FIELD OF THE INVENTION

The present invention relates to a novel anti-ferroelectric liquid crystal compound having an anti-ferroelectric phase in a broad temperature range and having a low melting point.

PRIOR ART

Liquid crystal display devices have been so far adopted mainly to various small-sized display devices owing to their operability at low voltage, low power consumption and performance of display with a thin screen. However, with recent increase in the application and use of liquid crystal display devices to/in the fields of information and office automation-related machines and equipment and the field of television sets, there are rapidly increasing demands for large-sized and high performance liquid crystal display devices having larger display capacity and higher display quality than those of conventional CRT display devices.

However, so long as a nematic liquid crystal available at present is used in a display device, even an active matrix driven liquid crystal display device (TFT) used in a liquid crystal television set has found it not easy to increase its size and decrease its production cost due to its complicated production process and a low yield. Further, in a simple matrix driven STN liquid crystal display device (STN), the driving of a large-capacity display device is not necessarily easy and its response time is limited, and hence, video frame rate display is difficult to obtain. At present, therefore, it cannot at all be said that the nematic liquid crystal display device can satisfy demands toward the above high-performance large-sized liquid crystal display device.

As for display quality, further, TFT and STN display devices using a nematic liquid crystal compound have a key problem in that the viewing angle is narrow. Though various solution methods have been proposed, it is difficult to find out a radical solution so long as a nematic liquid crystal compound is used.

Under the circumstances, a liquid crystal display device for which a ferroelectric liquid crystal compound is used is attracting attention as a liquid crystal display device with a fast response and a wide viewing angel. A surface-stabilized ferroelectric liquid crystal (SSFLC) device disclosed by Clark and Lagerwall comes under notice in that it has a fast response and a wide viewing angle which have not been achieved in the past. Its switching characteristics have been studied in detail, and a number of ferroelectric liquid crystal compounds have been synthesized for optimizing various physical property constants.

When a ferroelectric liquid crystal compound is used as a liquid crystal display device, however, a special devising with regard to the alignment of the liquid crystal is required for achieving a practically acceptable contrast, because its threshold characteristic is insufficient and its layer has a chevron structure. Further, since the alignment of its liquid crystal molecules is difficult to control, it is not easy to attain the bistability, which is one of the most important characteristics of SSFLC, with good reproducibility.

Further, there is another problem that when the alignment of the liquid crystal molecules is destroyed by mechanical shock, it is difficult to restore its alignment. It is therefore required to overcome these problems in order to put the device to practical use.

As described above, efforts have been made in various ways to develop novel modes for increasing the size of a liquid crystal display device and achieving a display with finer definition. Under the circumstances, development of devices having switching mechanisms which are completely different from the prior devices is also under way. Switching among tristable states of a liquid crystal compound having an anti-ferroelectric phase (to be referred to as "anti-ferroelectric liquid crystal compound" hereinafter) is one of these new switching mechanisms (Japanese Journal of Applied Physics, Vol. 27, pp. L729, 1988).

The anti-ferroelectric liquid crystal device has three stable states, i.e., two uniform states (Ur, Ul) observed in a ferroelectric liquid crystal device and a third state. Chandani et al report that the above third state is an anti-ferroelectric phase (Japanese Journal of Applied Physics, vol. 28, pp. L1261, 1989, Japanese Journal of Applied Physics, vol. 28, pp. L1265, 1989).

The above switching among tristable states is the first characteristic of an anti-ferroelectric liquid crystal device.

The second characteristic of the anti-ferroelectric liquid crystal device is that a sharp threshold value exists in respect to an applied voltage.

Further, the anti-ferroelectric liquid crystal device has a memory effect, which is the third characteristic of the anti-ferroelectric liquid crystal device.

The above excellent characteristics serve to achieve a liquid crystal display device having a fast response and a good contrast.

The anti-ferroelectric liquid crystal has another important characteristic in that its layer structure easily performs switching when an electric field is applied (Japanese Journal of Applied Physics, Vol. 28, pp. L119, 1989, Japanese Journal of Applied Physics, vol. 29, pp. L111, 1990).

On the basis of the above characteristics, a liquid crystal display device almost free of defects and capable of self-restoring a molecule alignment can be produced, and a liquid crystal device having an excellent contrast can be achieved.

As an anti-ferroelectric liquid crystal compound, there are known compounds disclosed in JP-A-1-213390, JP-A-1-316339, JP-A-1-316367, JP-A-1-316372, JP-A-2-28128 and "Liquid Crystals", Vol. 6, pp. 167 (1989). The number of anti-ferroelectric liquid crystal compounds which have been so far known is not so large as that of ferroelectric liquid crystal compounds, while anti-ferroelectric liquid crystal compounds are increasing in number with the advance in studies thereof.

In the field of ferroelectric liquid crystal compounds, attempts are being energetically made to synthesize ferroelectric liquid crystal compounds from the following alcohols in which a fluoroalkyl group is substituted on an asymmetric carbon atom (C*), as an optically active source for the synthesis (e.g., JP-A-64-3154, JP-A-1-316339, JP-A-1-316367, JP-A-1-316372, JP-A-2-225434 and JP-A-2-229128).

(1) $CF_3C^*H(OH)CH_2COOC_2H_5$ (2) $CF_3C^*H(OH)CH_2CH_2OC_2H_5$ (3) $CF_3C^*H(OH)CH_2CH_2CH_2OC_2H_5$ (4) $CF_3C^*H(OH)C_6H_{13}$ (5) $CF_3C^*H(OH)C_8H_{17}$ (6) $C_2F_5C^*H(OH)C_8H_{17}$

All of ferroelectric liquid crystal compounds derived from the above alcohols give high spontaneous polarization and also give a relatively fast response since a fluoroalkyl group having a high electronegativity is substituted on the asymmetric carbon atom. Further, it is also known that liquid crystal compounds derived from the above alcohols (4), (5) and (6) easily give liquid crystal compounds having an anti-ferroelectric phase or a ferrielectric phase.

On the other hand, the requirements of a liquid crystal compound in view of practical use are that the liquid crystal has an anti-ferroelectric phase in a broad temperature range and has a low melting point.

The present invention has been made from the above viewpoint, and it has been found that a biphenyl ester-containing liquid crystal compound obtained from a specifically structured optically active alcohol having a trifluoromethyl group on an asymmetric carbon atom and a fluoroalkyl group at a terminal gives an anti-ferroelectric liquid crystal compound having an anti-ferroelectric phase in a broad temperature range and having a low melting point.

According to the present invention, there is provided an anti-ferroelectric liquid crystal compound of the formula (1),

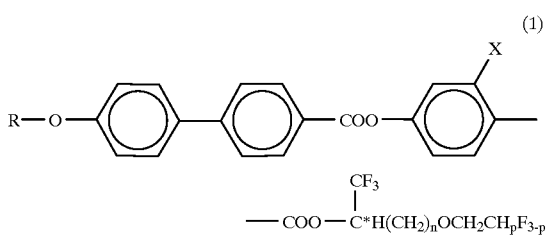

wherein R is a linear alkyl group having 6 to 12 carbon atoms, X is a hydrogen atom or a fluorine atom, n is an integer of 2 to 7, p is an integer of 0 to 2 and C* is an asymmetric carbon atom.

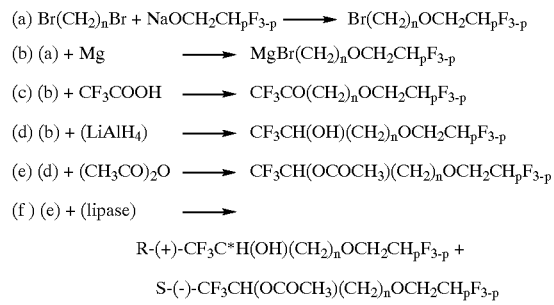

The above reaction scheme will be briefly explained as follows.

(a) shows the preparation of an ether compound by reacting alkyl bromide with sodium alkyl oxide.

(b) shows the preparation of a Grignard reagent.

(c) shows the carbon-propagation reaction based on a reaction between the Grignard reagent and trifluoroacetic acid.

(d) shows the reduction of a ketone.

(e) shows the acetylation of a racemic alcohol with anhydrous acetic acid.

(f) shows the hydrolysis of an acetate with lipase for optical resolution.

The anti-ferroelectric liquid crystal compound of the present invention can be produced from the above optically active alcohol according to the method which the present inventors already proposed (JP-A-3-292388).

The production method will be outlined as follows.

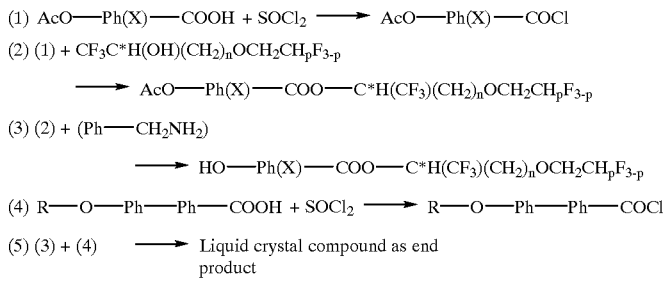

DETAILED DESCRIPTION OF THE INVENTION

The anti-ferroelectric liquid crystal compound of the present invention has the above formula (1). In the formula (1), R is a linear alkyl group having 6 to 12 carbon atoms, preferably a linear alkyl group having 9 carbon atoms. X is a hydrogen atom or a fluorine atom. n is an integer of 2 to 7, preferably 5. Further, p is an integer of 0 to 2, preferably 0 or 2, particularly preferably 2.

The optically active alcohol used for the synthesis of the above anti-ferroelectric liquid crystal compound of the present invention can be easily produced by the method which the present inventors already proposed. That is, the production method will be outlined as follows.

wherein Ac is an acetyl group, —Ph— is a 1,4-phenylene group, —Ph(X)— is a 1,4-phenylene group which may have a substituted fluorine atom on the 3-position, Ph— is a phenyl group, and C* is an asymmetric carbon atom.

The above production method will be briefly explained as follows.

(1) shows the chlorination of p-acetoxybenzoic acid with thionyl chloride.

(2) shows the formation of an ester by a reaction between the chloride (1) and the optically active alcohol.

(3) shows the deacetylation of the ester (2).

(4) shows the chlorination of 4'-alkyloxybiphenyl-4-carboxylic acid.

(5) shows the production of a liquid crystal compound by a reaction between the phenol (3) and the chloride (4).

EXAMPLES

The present invention will be explained more in detail with reference to Examples hereinafter, while the present invention shall not be limited to these Examples.

Example 1

(Preparation of (E1) R-(+)-3-fluoro-4-(1-trifluoromethyl-6-(2-fluoroethoxy)-hexyloxycarbonyl)phenyl=4-(4'-n-nonyloxybiphenyl)carboxylate; R=$CH_9H_{19}$, n=5, p=2, X=F in the formula (1))

(1) Preparation of 4-(4'-n-nonyloxybiphenyl)carboxylic acid

10 Grams of 4-(4'-hydroxybiphenyl)carboxylic acid and 14.0 g of n-nonyl bromide were added to a mixture containing 1,500 ml(milliliters) of ethanol and 200 ml of water, and the mixture was allowed to react under reflux for 10 hours. 500 ml of water was further added thereto, and the mixture was stirred for 3 hours. After completion of the reaction, the reaction mixture was acidified by adding concentrated hydrochloric acid, 500 ml of the solvent was distilled off, and the residue was cooled to a room temperature to give a white solid.

The white solid was fully washed with water and then recrystallized from chloroform, to give 14.0 g of an intended product in the form of a white crystal.

(2) Preparation of 4-acetoxy-2-fluorobenzoic acid

6 Grams of 4-hydroxy-2-fluorobenzoic acid and 8.2 g of anhydrous acetic acid were placed in a two-necked flask, and mixed. While the mixture was cooled with water, 5 drops of sulfuric acid were added. After heat generation was terminated, the mixture was heated at 80° C. for 30 minutes. Then, the reaction mixture was poured into cold water, and a precipitated crystal was recovered by filtration. The crystal was vacuum-dried, and used in the next step. The yield of the crystal was 4.8 g.

(3) Preparation of R-(+)-4-acetoxy-2-fluoro-1-(1-trifluoromethyl-6-(2-fluoroethoxy)-hexyloxycarbonyl) benzene 2.3 Grams of 4-acetoxy-2-fluorobenzoic acid was added to 10 ml of thionyl chloride, and the mixture was allowed to react under reflux for 5 hours. Then, excessive thionyl chloride was distilled off, and then a mixture containing 1 ml of pyridine, 4 ml of dry ether and 1.9 g of R-(+)-1,1,1-trifluoro-2-hydroxy-7-(2-fluoroethoxy)-heptane was dropwise added. After the dropwise addition, the mixture was stirred at room temperature for 24 hours and diluted with 200 ml of ether, and an organic layer was consecutively washed with diluted hydrochloric acid, with a 1N sodium hydroxide aqueous solution and with water, and dried over magnesium sulfate.

The solvent was distilled off, and the residue was purified by a silica gel column chromatography using hexane/ethyl acetate as a solvent, to give 1.3 g of an end product.

(4) Preparation of R-(+)-3-fluoro-1-hydroxy-4-(1-trifluoromethyl- 6-(2-fluoroethoxy)-hexyloxycarbonyl) benzene 1.0 Gram of the compound obtained in the above (3) was dissolved in 30 ml of ethanol, and 3 g of benzylamine was dropwise added. Further, the mixture was stirred at room temperature for 24 hours, then diluted with 300 ml of ether, consecutively washed with diluted hydrochloric acid and with water, and dried over magnesium sulfate.

The solvent was distilled off, and the residue was subjected to silica gel column chromatography for separation and purification, to give 0.6 g of an end product.

(5) Preparation of 4-(4'-nonyloxybiphenyl)carboxylic acid chloride

A large excess of thionyl chloride was added to 10 g of 4-(4'-n-nonyloxybiphenyl)carboxylic acid obtained in the above (1), and the mixture was refluxed for 5 hours. Excessive thionyl chloride was distilled off to give a crude end compound.

(6) Preparation of R-(+)-3-fluoro-4-(1-trifluoromethyl-6-(2-fluoroethoxy)-hexyloxycarbonyl)phenyl=4-(4'-n-nonyloxybiphenyl)carboxylate 0.7 Gram of the crude 4-(4'-nonyloxybiphenyl)carboxylic acid chloride obtained in the above (5) and 0.5 g of the phenol derivative obtained in the above (4) were dissolved in 25 ml of toluene, 3 ml of pyridine was added thereto, and the mixture was stirred at room temperature for 24 hours. The reaction mixture was diluted with 150 ml of dichloromethane, washed with a 1N hydrochloric acid aqueous solution, with a 1N sodium hydroxide aqueous solution and with water, and dried over anhydrous sodium sulfate, and the solvent was distilled off.

The resultant crude product was purified by silica gel column chromatography (hexane/ethyl acetate=9/1) to give 0.2 g of a liquid crystal compound as an end product.

Table 1 shows 1H-NMR data of the liquid crystal compound obtained in Example 1, and the liquid crystal compound was shown by the formula (E1).

The liquid crystal compound was identified for phases by texture observation and measurement with DSC (differential scanning calorimeter), and Table 2 shows the results. Further, melting points were determined with DSC. Table 2 shows the results.

TABLE 1

| 1H-NMR data of E1 of Example 1 | | | | | | | | | | |
|---|---|---|---|---|---|---|---|---|---|---|
| Hydrogen atom No. | 1 | 2 | 3 | 4 | 5 | 6 | 7 | 8 | 9 | 10 |
| E1 (δ, ppm) | 4.0 | 7.0 | 7.6 | 7.8 | 8.2 | 7.2 | 7.2 | 8.1 | 5.6 | 1.4 |

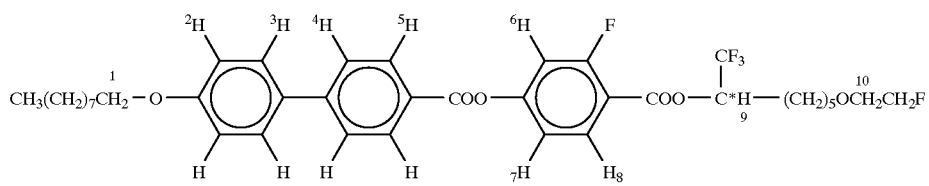

TABLE 2

| | Phase sequence | |
|---|---|---|
| Example 1 (E1) | Cr(<-41)SCA*(72)I | |

In the above Table 2, parenthesized values show transition temperatures (° C.), Cr is a crystal phase, SCA* is an anti-ferroelectric phase, and I is an isotropic phase.

The present invention provides novel anti-ferroelectric liquid crystal compounds. The novel anti-ferroelectric liquid crystal compounds provided by the invention have an anti-ferroelectric phase in a broad temperature range and have a low melting point, so that they can be advantageously used as a main component for a practical liquid crystal material or as a component for a liquid crystal composition.

What is claimed is:

1. An anti-ferroelectric liquid crystal compound of the formula (1),

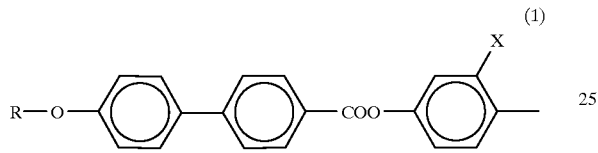

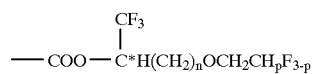

wherein R is a linear alkyl group having 6 to 12 carbon atoms, X is a hydrogen atom or a fluorine atom, n is an integer of 2 to 7, p is an integer of 0 to 2 and C* is an asymmetric carbon atom.

2. The anti-ferroelectric liquid crystal compound of claim 1, wherein R in the formula (1) is a linear alkyl group having 9 carbon atoms.

3. The anti-ferroelectric liquid crystal compound of claim 1, wherein n in the formula (1) is 5.

4. The anti-ferroelectric liquid crystal compound of claim 1, wherein p in the formula (1) is 0 or 2.

* * * * *